(12) United States Patent
Hoyle et al.

(10) Patent No.: US 8,440,736 B2
(45) Date of Patent: May 14, 2013

(54) PHOTOCUABLE THIOL-ENE LOW GAS PERMEABILITY MEMBRANES

(75) Inventors: Charles E. Hoyle, Hattiesburg, MS (US); Sergei Nazarenko, Hattiesburg, MS (US); Huanyu Wei, Fair Lawn, NJ (US)

(73) Assignee: University of Southern Mississippi, Hattiesburg, MS (US)

( * ) Notice: Subject to any disclaimer, the term of this patent is extended or adjusted under 35 U.S.C. 154(b) by 772 days.

(21) Appl. No.: 12/419,013

(22) Filed: Apr. 6, 2009

(65) Prior Publication Data

US 2009/0253805 A1    Oct. 8, 2009

Related U.S. Application Data

(60) Provisional application No. 61/042,920, filed on Apr. 7, 2008.

(51) Int. Cl.
| | |
|---|---|
| *B32B 17/10* | (2006.01) |
| *C08G 18/67* | (2006.01) |
| *C07C 381/00* | (2006.01) |
| *C07C 323/00* | (2006.01) |
| *C07C 321/00* | (2006.01) |
| *C07C 319/00* | (2006.01) |

(52) U.S. Cl.
USPC ............... 522/180; 522/174; 568/61; 568/62; 568/63; 568/64; 568/65; 568/66; 568/67; 568/68; 568/69; 568/70; 568/71; 568/72; 568/73

(58) Field of Classification Search
USPC ................................ 522/180, 174; 568/61–73
See application file for complete search history.

(56) References Cited

U.S. PATENT DOCUMENTS

| | | | |
|---|---|---|---|
| RE28,554 E | | 9/1975 | Curler et al. |
| 3,976,553 A | * | 8/1976 | Larsen .............................. 522/97 |
| 4,340,707 A | * | 7/1982 | Quis et al. ........................ 522/14 |
| 4,668,713 A | * | 5/1987 | Woods et al. ................. 522/174 |
| 4,808,638 A | * | 2/1989 | Steinkraus et al. ............. 522/24 |
| 5,290,635 A | | 3/1994 | Matsumura et al. |
| 5,516,455 A | * | 5/1996 | Jacobine et al. ......... 252/299.01 |
| 5,977,276 A | | 11/1999 | Toh et al. |
| 6,172,140 B1 | | 1/2001 | Toh et al. |
| 6,248,850 B1 | | 6/2001 | Arai |
| 6,291,565 B1 | | 9/2001 | Kling et al. |
| 6,391,983 B1 | | 5/2002 | Bateman et al. |
| 6,818,680 B2 | * | 11/2004 | Shustack ....................... 522/134 |
| 7,169,825 B2 | * | 1/2007 | Narayan-Sarathy et al. ... 522/13 |
| 7,256,221 B2 | | 8/2007 | Coykendall et al. |
| 7,288,608 B2 | | 10/2007 | Bowman et al. |
| 7,709,545 B2 | * | 5/2010 | Hoyle et al. ..................... 522/14 |
| 7,709,555 B2 | * | 5/2010 | Stappers et al. .............. 522/176 |
| 7,838,571 B2 | * | 11/2010 | Bowman et al. ................ 522/44 |

OTHER PUBLICATIONS

Hoyle et al., "Thiol-Enes: Chemistry of the Past with Promise for the Future," Journal of Polymer Science: Part A: Polymer Chemistry, 42:5301-5338 (2004).

* cited by examiner

*Primary Examiner* — Ling Choi
*Assistant Examiner* — Jessica E Whiteley
(74) *Attorney, Agent, or Firm* — Butler, Snow, O'Mara, Stevens & Cannada PLLC

(57) ABSTRACT

The present invention provides modified multifunctional thiol-ene monomers wherein one or more thiols are reacted with a Michael addition reactive double bond compound. The present invention further discloses photocurable thiol-ene formulations comprising thiol-ene monomers including the modified multifunctional thiols. The present invention further discloses photocurable thiol-ene formulations comprising thiol-ene monomers and Michael addition reactive double bond molecules and a Michael catalyst. The formulations of the present invention can be photocured to make films or coatings. In a further disclosure, the formulations, including those comprised of unmodified multifunctional thiols and multifunctional enes, are photocured to form films applied to non-flexible or flexible polymer or non-polymer substrates suitable for food packaging, electronic products, optical products and other applications and free-standing films. The present invention further discloses photocurable thiol-ene formulations comprising thiol-ene monomers and Michael addition reactive double bond molecules and a Michael catalyst. These formulations are disclosed to form free-standing films and coatings on substrates when applied to flexible substrates. Such materials are suitable for use in the packaging of food products and other products which are to be maintained in a hermetically sealed relationship to the atmosphere.

4 Claims, No Drawings

_(1)_

PHOTOCUABLE THIOL-ENE LOW GAS PERMEABILITY MEMBRANES

This application claims benefit of priority from U.S. Provisional Application Ser. No. 61/042,920 filed Apr. 7, 2008, the entire content of which are incorporated by reference herein.

BACKGROUND OF THE INVENTION

One of the primary applications of plastics materials is food packaging where permeability to gasses such as oxygen is not desired. Oxygen and water are well know chemical reagents for reactions with food and other sensitive substrates. This severely reduces the packed materials service life. Polymer material ranging from polyesters based upon monomers such as terephthalic acid copolymerized with alkane diols to copolymers of ethylene and vinyl alcohol have been used as high oxygen (and other gas) barrier materials. Other polymers such as nylon, polyvinylidene dichloride, nylon and copolymers of maleic anhydride and acrylic acid also function as polymeric gas barrier materials. Uses of gas barrier films include packaging of food and liquids, electronics, pharmaceuticals, and chemicals. In general polymeric packaging materials are fabricated by processing polymeric materials into sheets or thin films, laminated of multiple pre-formed thin polymer films, injection molding, blow molding, compression molding, and other processes which require elevating preformed polymers to high temperatures followed by a cooling or series of cooling cycles. Alternatively, thermally cured coatings with barrier properties may be used to coat low barrier polymers.

Traditional coatings or films used to improve gas barrier on applied substrates involves long application and processing times often at high temperatures, thermoforming requiring expensive equipment, use of environmentally unfriendly solvents, and the problems caused by shrinking during the above processing steps. A successful UV cured coating that significantly improves the barrier resistance of substrate materials could reduce processing costs and processing times.

SUMMARY OF THE INVENTION

The present invention provides photocurable systems used to improve gas barriers on applied substrates. The photocurable systems provide distinct advantages as opposed to traditional laminate and thermoforming systems because of the relative ease in application and rapid curing of the film in place as applied. The present invention has discovered that UV-cured thiol-ene films in a wide variety of formats and combinations provide excellent substrate barrier resistance hat will reduce processing costs and processing times not readily achievable by alternative coating systems currently used in the art of barrier films. Note that thiol-enes include single multifunctional thiols or combinations of mixtures of monofunctional and multifunctional thiols and multifunctional enes or combinations of monofunctional enes and multifunctional enes the latter including carbon carbon double bond species and carbon-carbon triple bond species in the broadest sense. The thiol-ene networks are expected to be safe for food and other contact since they will be fully cured, or at least one of the functional groups on each multifunctional component will be incorporated into the final cured network, and the thiol and ene components are generally considered to be relatively non-toxic chemical components.

In one aspect, the present invention provides a modified or unmodified thiol for use in thiol-ene formulations comprising at least one multifunctional thiol and up to as many as ten or more multifunctional thiols of different structures wherein the thiol end groups are eventually photocured and reacted with an ene or a mixture of any number of ene compounds. In the modified thiol, double bonded carbons capable of undergoing Michael addition reactions hereafter referred to as Michael addition reactive double bond species are reacted with at least one of the thiols by the Michael addition process. In the modified thiol, the multifunctional thiol used to synthesize the modified multifunctional thiol is preferably pentaerythritol tetra-(3-mercaptopropionate) (TetraThiol1), ethoxylated pentaerythritol tetra-(3-mercaptopropionate) (Tetra-Thiol1), trimethylpropane tri(3-mercapto-propionate) (TriThiol1), glycol 3-mercaptopropionate, poly propylene glycol 3-mercaptopropionate, ethoxylated trimethylpropane tri(3-mercapto-propionate) (TriThiol2), ethoxylated glycol dimercaptoacetate, trimethylolpropane trimercaptoacetate, glycol di-(3-mercaptopropionate), 1,4-bis (3-mercaptobutyloxy) butane, pentaerithrytol tetrakis (3-mercaptobutylate), or 1,3,5-Tris(3-melcaptobutyloxethyl)-1,3,5-triazine-2,4,6 (1H,3H,5H)-trione. Other related thiols are also envisioned as well as including secondary thiols and other multifunctional thiols synthesized by other methodologies. In another aspect, the modified thiol is used in a photopolymerizable thiol-ene formulation containing a photoinitiator where the ene compounds include monofunctional and multifunctional single enes or mixtures of enes such that the average functionality of the mixture is 2 or more functional groups taken from any ene or set of enes including but not limited to norbornenes, vinyl ethers, vinyl esters, N-vinyl amides, allyl ethers, allyltriazines, allylisocyanurates, alkenes, $\alpha,\beta$-unsaturated esters, N-substituted maleimides, acrylonitriles, styrenes, conjugated and non-conjugated dienes, fumaronitrile, acrylamide, (meth)acrylates (mono(meth)acrylates, (meth)acrylates, acrylamides, acetonitrile, fumaramides, maleamides, (meth)acrylic acid, maleic anhydride, or alkynes herein defined as a double ene with two enes on the same two carbon atoms. The photopolymerizable network typically will have the thiol and the ene monomers present in a 1:1 molar ratio, although it can be formulated and cured in a variety of different of stochiometric ratios ranging to give films which will show barrier properties.

In another aspect of the invention, a photopolymerizable formulation comprising a multifunctional thiol, an ene monomer or monomers, a photoinitiator, an amine or other Michael catalyst and fumaronitrile is used. The ene compounds include monofunctional and multifunctional single enes or mixtures of enes such that the average functionality of the mixture is 2 or more functional groups taken from any ene or set of enes including but not limited to norbornenes, vinyl ethers, vinyl esters, N-vinyl amides, allyl ethers, allyltriazines, allylisocyanurates, alkenes, $\alpha,\beta$-unsaturated esters, N-substituted maleimides, acrylonitriles, styrenes, conjugated and non-conjugated dienes, fumaronitrile, acrylamide, (meth)acrylates (mono(meth)acrylates, (meth)acrylates, acrylamides, acetonitrile, fumaramides, maleamides, (meth)acrylic acid, maleic anhydride, or alkynes herein defined as a double ene with two enes on the same two carbon atoms. The photopolymerizable formulation typically will have the thiol and ene monomers present in a 1:1 molar ratio, although it can be formulated and cured in a variety of different of stochiometric ratios ranging to give films which will show barrier properties.

Further, a free-standing film of photopolymerizable formulations is also contemplated as part of the present invention. The present invention also provides a barrier material for use in the packaging of food products and other products which are to be maintained in a hermetically sealed relationship to the atmosphere. In another embodiment of the invention, the barrier material is a product prepared by mixing a photoinitiator with a photopolymerizable formulation; applying the photopolymerizable formulation to a substrate suitable for being used as a base matrix for flexible food packaging; and curing the formulation with UV light. The use of a photoinitiator is optional for thiol-ene systems since direct exposure to UV light is capable of mixing thiol-ene systems with no photoinitiator present. Since photoinitiator fragments and unreacted photoinitiator can remain in the photocured thiol-ene network film, a second embodiment of the invention is to process thiol-ene systems in the absence of added photinitiator or with non-migratable photoinitiators. All combinations of thiol and enes including multifunctional thiols and multifunctional enes as defined herein, modified multifunctional thiols and multifunctional enes and three component systems where multifunctional thiols, multifunctional enes and a third component selected from Michael reactive double bonded species with the general structure ABC=CDE with preferable at least one of the substitutent groups ABDE being an electron withdrawing group such as —COOR, —CONHR, —Cl or other halogen, —CtriplebondN, or an alcohol are envisioned as photopolymerizable formulations for preparation of films on flexible polymer materials suitable for food packaging including but not limited to paper, wax paper, polyethylene, polyethyleneterephthalate, and polypropylene. For —COOR and —CONHR, R can be H, an alkyl group, or any group with electron withdrawing power such as a halogen, cyano, amide, carboxylic acid, carboxylic ester, or other species know by practitioners in the trade.

In one embodiment, the invention is directed to a modified tetrathiol comprising pentaerythritol tetrakis(3-mercaptopropionate) ("TetraThiol1") modified by a Michael addition reactive double bond. For synthesis of the modified thiol, Michael reactive double bonded species with the general structure ABC=CDE with preferable at least one of the substitutent groups ABDE being an electron withdrawing group such as —COOR, —CONHR, —Cl or other halogen, —CtriplebondN, or an alcohol. R can be H, an alkyl group, or any group with electron withdrawing power such as a halogen, cyano, amide, carboxylic acid, carboxylic ester, or other species known by those skilled in the art. In another embodiment, the invention is directed to a photopolymerizable thiol-ene formulation comprising the modified tetrathiol and 1,3,5-Triallyl-1,3,5-triazine-2,4,6(1H,3H,5H)-trione (TTT). In a further aspect, the photopolymerizable thiol-ene formulation is used to make a film. Such films find application as barrier materials particularly suitable for use in the packaging of food products and other products which are to be maintained in a hermetically sealed relationship to the atmosphere.

In another embodiment, the invention is a photopolymerizable thiol-ene formulation comprising: pentaerythritol tetrakis(3-mercaptopropionate) combined with 1,3,5-triallyl-1,3,5-triazine-2,4,6(1H,3H,5H)-trione (TTT) and either acrylonitrile, or other monomer units such as dichloroethylene, (meth)acrylic acid, fumaramide, maleamide, or other monomer with groups know to those skilled in the art to reduce oxygen transport.

The films of the present invention can be used as a barrier material particularly suitable for use in the packaging of food products and other products which are to be maintained in a hermetically sealed relationship to the atmosphere. The photocurable liquid thiol-ene formulations can be applied to a substrate safe for packaging including polyethyleneterephthalate, other polyesters, polyamides, and polyolefins such as polyethylene and polypropylene, and cured with UV light. The photocurable thiol-ene liquid may also be incorporated and cured to give a film to film adhesive layer joining polyolefins, polyamides, polyesters and the like.

DETAILED DESCRIPTION OF THE INVENTION

One aspect of the invention provides modified multifunctional thiol. The modified thiol of the present invention features a thiol structure wherein at least one but not all of the thiol end groups are reacted with a Michael addition reactive double bond. In another aspect, a photopolymerizable formulation involving a multifunctional thiol, an ene monomer or monomers, a photoinitiator, an amine or other Michael catalyst and fumaronitrile is envisioned. Alternately other ene monomers can be used that will provide enhanced oxygen and other gas barrier properties such as acrylonitrile, fumaramide, maleimide, acrylamide, hydroxyl alkyl acrylate, (meth)acrylic acid and other monomers know to practitioners skilled in the art. In another aspect, photocurable barrier films will be made from non-modified multifunctional thiol and multifunctional ene formulations. The multifunctional thiols used in all embodiments are described in [0011].

Thiol Structure

The three types of multifunctional thiols used are alkyl thiols, thiol glycolate esters and thiol propionate esters. A tri- or tetra- multifunctional thiol is preferred for the purposes of this invention. Structures, formal names, and acronyms for several of the commercially available multifunctional thiols are given in U.S. Pat. No. 6,391,983, incorporated by reference herein.

The two most widely used and commercially available thiols, pentaerythritol tetra(3-mercaptopropionate) (designated TetraThiol1, structure given in Chart 1 below) and trimethylolpropane tri(3-mercaptopropionate) (designated TriThiol1, see Chart 1) are based upon reactions of mercaptopropionic acid with trimethyol propane and pentaerythritol, respectively. Thiols TriThiol2 and TetraThiol4, also given in Chart 1, are based upon reactions of mercaptopropionic acid with ethoxylated trimethylol propane and ethoxylated pentaerythritol are also available commercially, as is TriThiol3 in Chart 1. TriThiol2, TetraThiol2, and TriThiol3 are touted as low odor thiols. TetraThiol3 in Chart I is a four functional thiol containing two 3-mercaptopropionate groups and two 2-mercaptopropionate groups with differing reactivity.

CHART 1

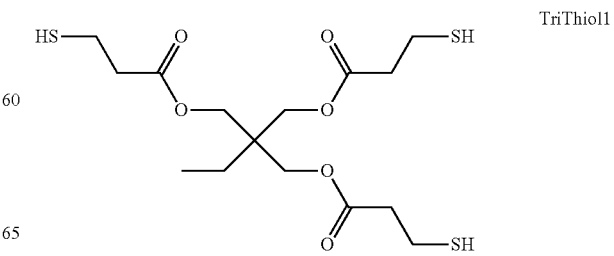

TriThiol1

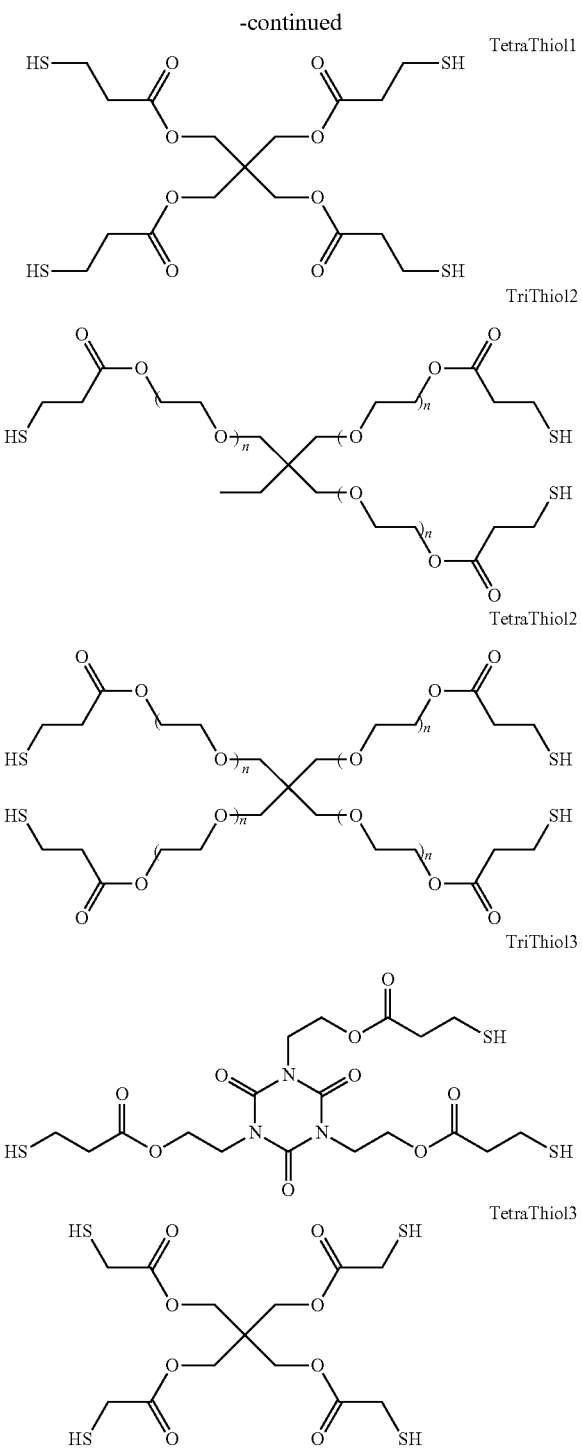

In addition to the multifunctional thiols (shown in Chart 1), others have been reported that may well be useful in a variety of applications. Wood et al., U.S. Pat. No. 5,459,175, incorporated herein by reference, reported synthesis of thiols via a process in which an excess of thiol was added to a dinorbornene by a free-radical chain process. In the presence of an azo thermal initiator which produces free-radicals, the thiol added to the dinorbornene to give a hexafunctional thiol referred to as HexaThiol. The synthesis of this hexafunctional thiol is particularly interesting since it provides a rationale for the general synthesis of highly functional thiols by a thermal free-radical chain process. For example, the tertafunctional thiol could be added to the tri- and tetrafunctional norbornenes synthesized by Woods, Jacobine and coworkers to give nine and twelve functional thiols. And, this method is not limited to norbornenes, since it should be possible to also use multifunctional allyl ethers, vinyl ethers, and other multifunctional monomers. This would provide for synthesis of an abundant number of multifunctional thiols with a wide variance in the chemical structure of the backbone separating the thiol groups. According to Woods and Jacobine, HexaThiol and similar multifunctional thiols can be mixed with virtually any multifunctionality monomer that it is miscible with in order to adjust the gel point of the polymerization process. The functionality of the thiol, while not being exactly 6.0 due to impurities, as discussed in the patent, is still close, and will therefore gel when photopolymerized with a given functional ene at a much lower functional group conversion. Such higher functional thiols might be expected to cure very rapidly in thiol-ene reactions while giving rise to some unusual architectures. Also, since the choice of the ene to copolymerize with these new multifunctional thiols is essentially endless, it should be possible to tailor molecular composition of films in a way heretofore unobtainable. Finally, a recently synthesized hyperbranched 16 functional thiol, designated SixteenThiol, has been described by workers at Perstorp. Other thiols can be synthesized by Michael addition reactions between multifunctional thols and electron deficient multifunctional enes such as (meth)acrylates, amides, unsaturated esters based on fumaric acid and maleic acid, and others enes known to those skilled in the art.

Ene Structure

In accordance with the present invention, enes of the present invention feature a compound containing an average of two or more carbon-carbon double bond —C=C—. These carbon-carbon double bond compounds include monofunctional and multifunctional single enes or mixtures of enes such that the average functionality of the mixture is 2 or more functional groups taken from any ene or set of enes including but not limited to norbornenes, vinyl ethers, vinyl esters, N-vinyl amides, allyl ethers, allyltriazines, allylisocyanurates, alkenes, α,β-unsaturated esters, N-substituted maleimides, acrylonitriles, styrenes, conjugated and non-conjugated dienes, acrylamide, multi(meth)acrylates, mono(meth)acrylates, (meth)acrylic acid, acrylamides, acetonitrile, fumaronitrile, fumaramides, maleamides, acrylic acid, maleic anhydride, alkynes herein defined as a double ene with two enes on the same two carbon atoms, and other enes known to practitioners skilled in the art.

Michael Addition Reactive Double Bond

For synthesis of the modified thiol, Michael reactive double bonded species with the general structure ABC=CDE with preferable at least one of the substitutent groups ABDE being an electron withdrawing group such as —COOR, —CONHR, —Cl or other halogen, —CtriplebondN, or an alcohol. R can be H, an alkyl group, or any group with electron withdrawing power such as a halogen, cyano, amide, carboxylic acid, carboxylic ester, or other species known by those skilled in the art. Examples include famaramides, maleamides, acrylinitrile, funaronitrile, (meth)acrylic acid, acrylate derivatives with acid functionalities, (meth)acrylates, dichloroethylene, acrylamides, and other electron deficient carbon-carbon double bonds known to practitioners in the art.

In an embodiment, the invention is directed to a photopolymerizable formulation comprising the modified multifunctional thiol and an ene (such as for example 1,3,5-Triallyl-1,3,5-triazine-2,4,6(1H,3H,5H)-trione (TTT)) mixed in a 1:1 molar ratio. In a further aspect, the photopolymerizable formulation is used to make a film on a non-flexible sensitive substrate for electronic or optical applications or a flexible substrate suitable in food packaging applications such as polyethylene, polyethyleneterephthalate, or polypropylene. Such films find application as barrier materials particularly suitable for use in the packaging of food products and electronic, optical or other products which are to be maintained in a hermetically sealed relationship to the atmosphere.

In another embodiment, the invention is a photopolymerizable formulation comprising a multifunctional thiol (e.g. pentaerythritol tetrakis(3-mercaptopropionate)) combined with an ene monomer (such as 1,3,5-triallyl-1,3,5-triazine-2,4,6(1H,3H,5H)-trione (TTT)) and a second ene (e.g. acrylonitrile). The components are added at a 1:1:2 molar ratio of thiol: TTT: acrylonitrile. In a further aspect, the photopolymerizable formulation is used to make a film or coating.

In another embodiment, the invention is a photopolymerizable formulation comprising pentaerythritol tetrakis(3-mercaptopropionate) combined with 1,3,5-triallyl-1,3,5-triazine-2,4,6(1H,3H,5H)-trione and fumaronitrile added at a 1:1:1 molar ratio of thiol: TTT: fumaronitrile with a catalytic amount of an amine Michael addition catalyst. In a further aspect, the photopolymerizable formulation is used to make a film. This particular film has oxygen barrier properties rivaling those of the best polymers and exhibits unique characteristics to function as an oxygen sensor. As the film is exposed to oxygen over time the film changes color: going from a light yellow, to green, and then to opaque black.

In one aspect, the present invention is directed to thiol-ene based formulated coatings and thermosets that can be applied in the liquid form to various substrates used in preparing food packaging products. Examples of substrates that can be used in the invention include paper, wax, thermoplastic plastic thermosets or thermoplastics. The thiol-ene networks are expected to be safe for food contact since they will be fully cured, or at least one of the functional groups on each multifunctional component will be incorporated into the final cured network, and the thiol and ene components are generally considered to be relatively non-toxic chemical components. Application of the liquid formulation coating to the substrate is followed by a UV curing step that results in lowering the permeability of oxygen and other gases through the material, that is, a photocurable thiol-ene formulation based low permeable membrane protective film. The film may be applied by spraying, dip coating, roll coating, and other techniques widely recognized by those of skill in the art. The permeability of several types of materials currently used in the food packaging industry are given in Table 1 below. They are representative of films and materials typically used in the food packaging industry.

TABLE 1

Permeability values for several food packaging materials in cc(STPcm m$^{-2}$day$^{-1}$atm$^{-1}$

| | Polymer | | | |
|---|---|---|---|---|
| | Polyacrylonitrile-co-styrene (25° C.) | Polyvinylidene chloride (30° C.) | Nylon 6 (25° C.) | Polyethylene-terephthalate (PET) (30° C.) |
| Permeability | 0.028 | 0.034 | 0.249 | 0.389 or 0.48 |

In one embodiment, the photocurable formulations of the present inventions are pre-cured to a point just prior to gelation before application. Precuring can be accomplished because the thiol-ene systems of the present invention cure by a step-growth polymerization mechanism. A distinct advantage of this pre-curing is that it provides for shrinkage of the formulation while in the liquid state, thus limiting curing induced stress and shrinkage typical of other high solids coatings systems. It also provides the same advantages over other alternative photocured resins, such as multifunctional acrylates, which are prone to significant shrinkage upon curing and hence problems with stress buildup and substrate adhesion.

Selection of particular photoinitiators and optimization of the amount used can be easily achieved by one of skill in the art. In one preferred embodiment, alpha,alpha-dimethoxy-alpha-phenylacetophenone, or DMAP, is used as the photoinitiator. In one embodiment, the photoinitiator is used at 1 wt %. The photoinitiator range can range from 0 (thiols are capable of initiating their own polymerization) to up to 10 wt %. Since photoinitiator fragments and unreacted photoinitiator can remain in the photocured thiol-ene network film, a second embodiment of the invention is to process thiol-ene systems in the absence of added photinitiator. Any photoinitiator used in the photocuring industry to generate radicals upon exposure to UV or visible light including type 1 initiators such as but not limited to alpha cleavable photoinitiators such as substituted acetophenones, benzoin ethers, amino ketones, phosphine oxides and type 2 abstraction photoinitiators and their derivatives such as benzophenones, thioxanthones, and benzils and the like can be used. Or alternatively systems with no photoinitiator can be used, since thiols are readily photoactive in the absence of additional photoinitiator.

Table 2 lists gas barrier results for thiol-ene and thiol-yne photocured films made by exposing the formulations, provided in the examples herein, to high intensity UV light. For comparison, results for biaxially-oriented polyethylene-terephthalate (Mylar), a traditional material used to limit permeability of oxygen into food and liquids, are included. Oxygen permeability tests conducted at room temperature and 0% RH using Mocon OX-TRAN 2/21 device. Water vapor permeability tests conducted at room temperature and 100% RH using Mocon PERMATRAN-W 3/33 device. Table 2 provides the permeability of oxygen and water vapor through photocured thiol-ene based network films, reporting permeability for oxygen as measured in cc(STP) cm m$^{-2}$ day$^{-1}$ atm$^{-1}$ and permeability for water vapor as measured in g cm m$^{-2}$ day$^{-1}$. Permeability is the fundamental constant that determines the flux of gas through a membrane and is related to the product of the solubility and diffusion coefficient of a gas through a polymer [J. Crank, The Mathematics of Diffusion, Oxford University Press, London, pp. 44-46 (1975)] where the solubility of the gas is the ratio of the gas concentration in the film and the pressure of the gas in direct contact with the film and the diffusion coefficient is the ratio of mass transfer of the gas molecules per unit area to the concentration gradient.

TABLE 2

Oxygen and water permeability values for photocured thiol-ene based network films and control films

| Material | Oxygen Permeability (cc(STP) * cm * $m^{-2} day^{-1} atm^{-1}$) Normal | Annealed | Water Vapor Permeability (g * cm * $m^{-2} day^{-1}$) |
|---|---|---|---|
| Trithiol1 + TEGDVE | 13.750 | — | — |
| Trithiol1 + APE | 1.600 | — | — |
| Trithiol1 + TOT | 0.220 | — | — |
| Trithiol1 + TTT | 0.090 | 0.100 | 0.042 |
| Tetrathiol1 + TTT (1:1) | 0.032 | 0.032 | 0.022 |
| Tetrathiol1 + TTT (4:3) | 0.041 | 0.042 | 0.042 |
| Trithiol3 + TTT | 0.021 | 0.024 | 0.018 |
| (Tetrathiol1-Ethyl acrylate)mod + TTT | 0.390 | 0.450 | — |
| (Tetrathiol1-Butyl acrylate)mod + TTT | 1.1 | — | — |
| (Tetrathiol1-Hexyl acrylate)mod + TTT | 2.06 | — | — |
| (Tetrathiol1-Acrylonitrile)mod + TTT | 0.090* | — | — |
| (Tetrathiol1-Hydroxyethyl acrylate)mod + TTT | 0.160 | 0.160 | 0.067 |
| (Tetrathiol1-Acrylamide)mod + TTT | 0.030 | 0.030 | 0.102 |
| TetraThiol1 + Fumaronitrile + TTT | 0.00013** | — | 0.039** |
| TetraThiol1 + Acrylonitrile + TTT | 0.059* | — | — |
| 1,4-Butanedithiol + octadiyne | 0.042 | — | 0.034 |
| Mylar PET | 0.146 | — | 0.020 |

All values unless otherwise noted are obtained for films made with a 5 mil drawdown bar at 50 $cm^2$ testing area.
Final film thicknesses ranged from 60 to 90 microns and were normalized at room temperature in air for a minimum of three days before testing.
*Obtained using 5 $cm^2$ testing area and 9 mil drawdown bar.
**Obtained using 50 $cm^2$ area and 20 mil drawdown bar. Also note this value is instrumentation limited.

EXAMPLES

Example 1

TriThiol+TTT Recipe and TetraThiol1+TTT Recipe

Trimethylolpropane tris(3-mercaptopropionate) ("TriThiol") is combined with 1,3,5-Triallyl-1,3,5-triazine-2,4,6(1H,3H,5H)-trione ("TTT") at a 1:1 molar ratio. 1 wt % photoinitiator (Alpha,alpha-dimethoxy-alpha-phenylacetophenone, abbreviated DMAP, sold as Irgacure® 651) is added to the mixture and then sonicated for 10 minutes or until solution is clear and free of bubbles. The mixture is then drawn down onto a glass plate at 200 micrometers thickness and cured using 10 passes at 10 ft/min feed speed under a Fusion UV curing line system with a D bulb (400 W/cm2) (Scheme 1). The cured films were analyzed by a Mocon OxTran 2/21 using ASTM D 3985-81 to assess the data. Samples of TriThiol+TTT were prepared and cured similarly followed by annealing at 90° C. (Schemes 2 and 3). TriThiol+TTT samples were also subjected to annealing at 90° C. in air to see if additional changes in the permeability occurred: no significant changes occurred for the TriThiol+TTT sample and therefore the results for the TetraThiol1+TTT annealed sample are comparable. Annealing has little effect (Scheme 2 and 3) in increasing the permeability significantly and hence is not an obstacle for use of the material where exposure to high temperatures may occur from time to time.

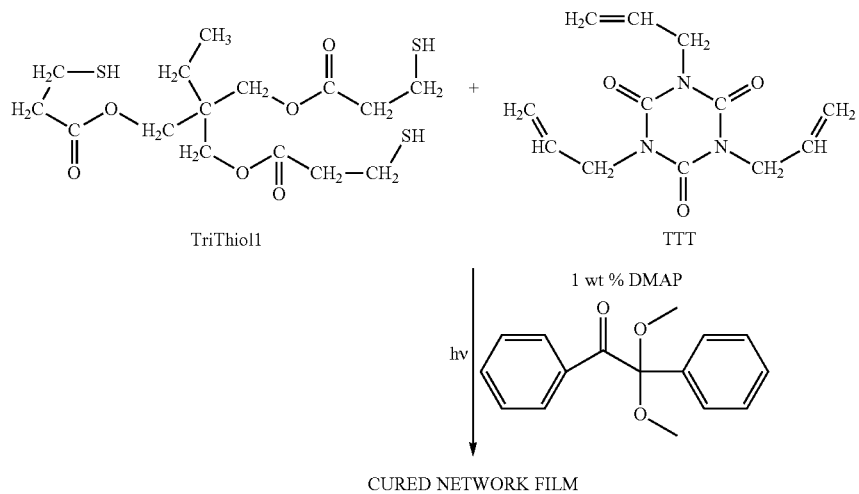

Scheme 1: (1 mol TriThiol1 + 1 mol TTT)

Scheme 2: (1 mol TriThiol1 + 1 mol TTT, annealed at 90 C.)

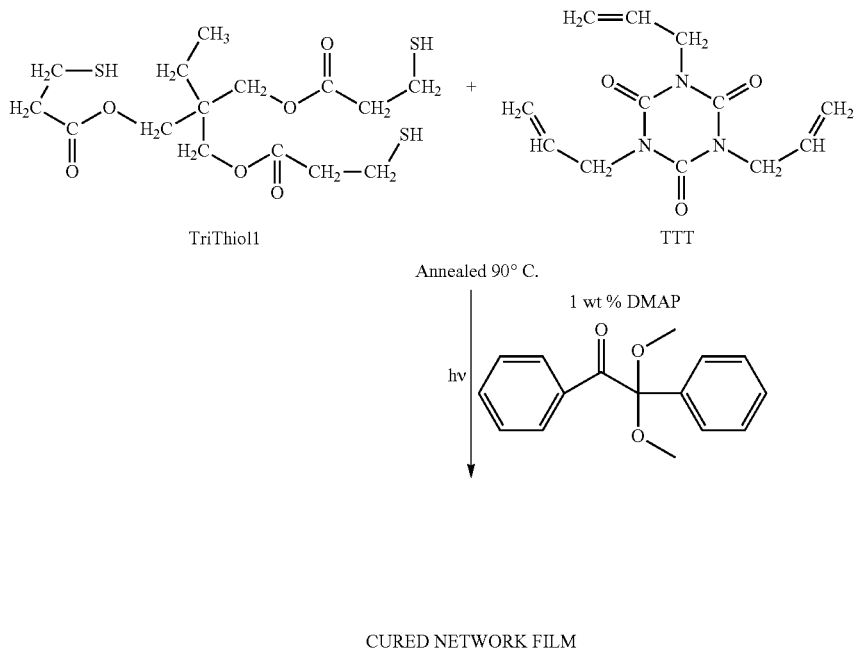

Scheme 3: (3/4 mole TetraThiol1 + 1 mol TTT, annealed at 90 C.)

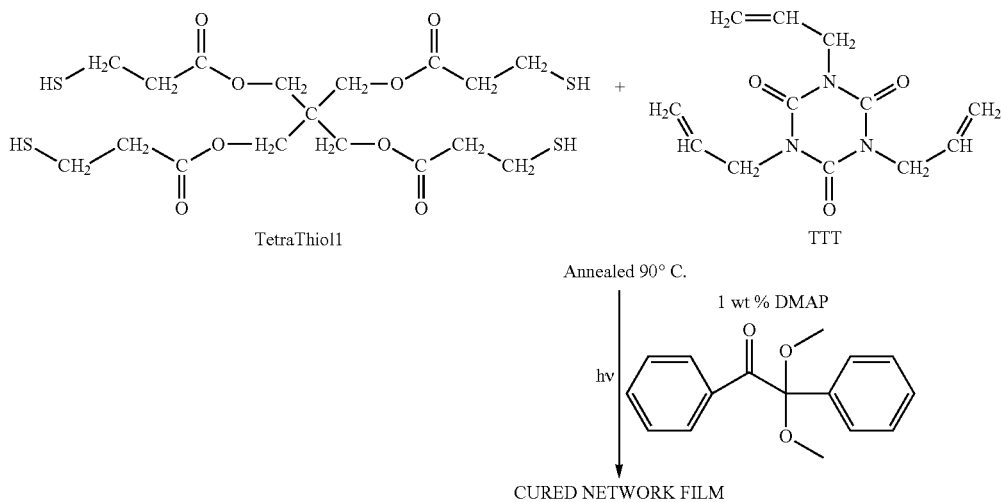

Example 2

Modified 4-Functional Thiol Synthesis and Modified TetraThiol (TetraThiol1)+TTT Photopolymerization.

The TetraThiol1 was reacted (Scheme 4) with a number of double bonds functionalized with groups (hydroxyethylacrylate, cyano, chloro, amide, alkylacrylates) designed to alter the properties of the thiol essentially creating totally new thiols of functionality 3 (average functionality of a statistical mixture) with the type of attached groups which are purported (or can be deduced to be) effective in altering the gas barrier properties of polymers. (Morris Salame, Polymer Engineering and Science, vol.26, pp. 1543-1546, 1987). The double bond functionalized may be acrylonitrile, acrylamide, hydroxyethylacrylate, dichloroethylene, fumaramide, maleamide, dicyanoethylene and the like with at least one strong electronic withdrawing groups attached to the —C═C— bond, with the general structure ABC═CDE with preferable at least one of the substituent groups ABDE being an electron withdrawing group such as —COOR, —CONHR, —Cl or other halogen, —CtriplebondN, or an alcohol and other electron deficient double bond compounds known to those skilled in the art to undergo Michael addition reactions.

Scheme 4: Synthesis of Modified Thiols

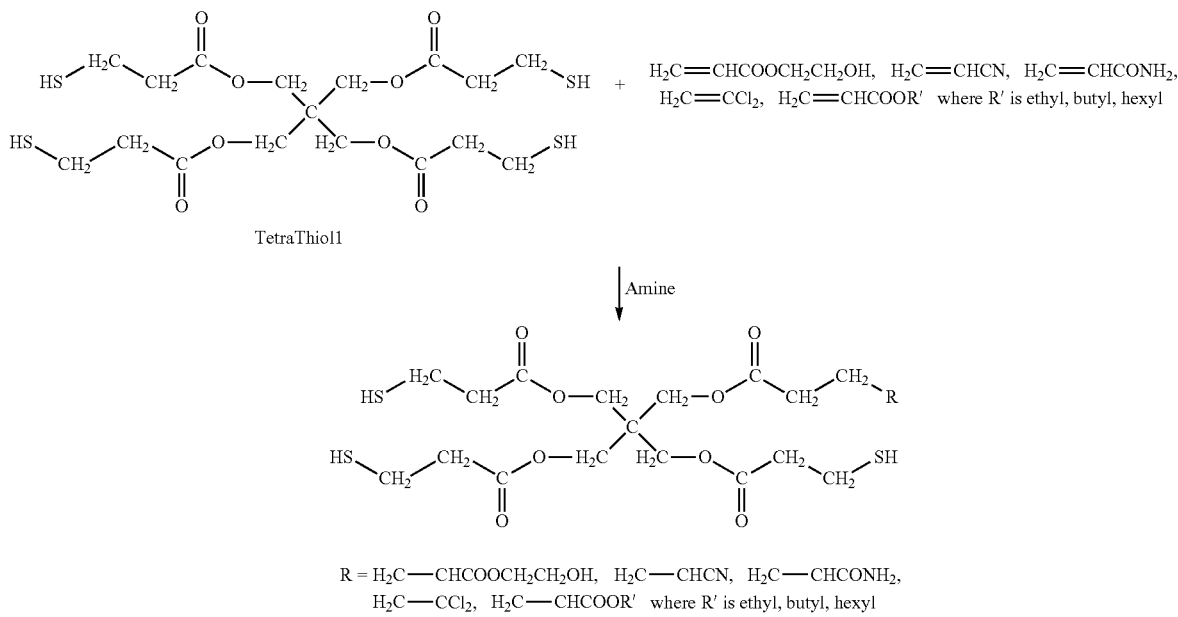

The modified compounds described in Scheme 4 are designated as (TetraThiol1+dichloroethane)$_{mod}$, (TetraThiol1+ethyl acrylate)$_{mod}$, (TetraThiol1+acrylonitrile)$_{mod}$, (TetraThiol1+butyl acrylate)$_{mod}$, (TetraThiol1+hexyl acrylate)$_{mod}$, and (TetraThiol1+hydroxyl ethyl acrylate)$_{mod}$ and (TetraThiol1+acrylamide)$_{mod}$. The end product is a thiol with average functionality of three with one of the thiols converted into a sulfide by an amine catalyzed conjugate reaction between the thiol and the electron deficient double bond.

(TetraThiol1+butyl acrylate) mod, (TetraThiol1+hexyl acrylate) mod, and (TetraThiol1+hydroxyl ethyl acrylate) mod were synthesized by the thiol Michael addition reaction. The modified thiol end product was then combined into a thiol-ene formulation and photocured with ene TTT in the presence of a photoinitiator and photocured as depicted in Scheme 5. The end product is a crosslinked thiol-ene type network where the thiols have reacted via a free-radical chain process with the ene groups to give sulfides and a network with high connec- Scheme 5: Photopolymerizable formulation and photocuring

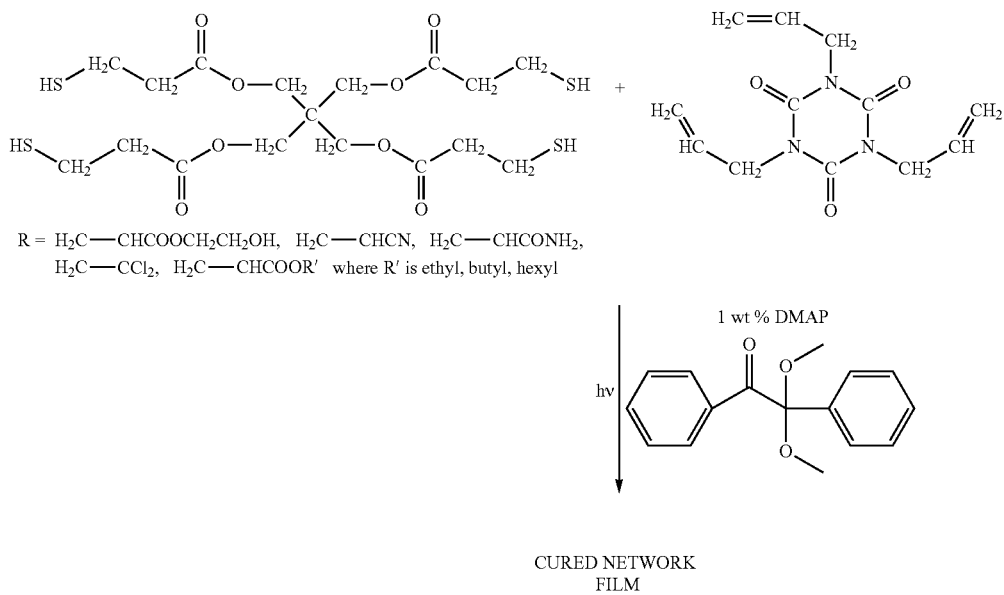

The modified compounds including (TetraThiol1+dichloroethane) mod, (TetraThiol1+ethyl acrylate)mod, tion density, i.e., high linking density. This process is described herein for two examples, acrylamide and acetonitrile. Similar procedures were used to prepare the other modified thiols and incorporate into photopolyomerizable formulations, and then photocured.

[TetraThiol1+Acrylamide]+TTT Recipe (tail-group modification): Pentaerythritol tetrakis(3-mercaptopropionate) ("TetraThiol1") is added to a round-bottom flask. An equal molar quantity of acrylamide is weighed out in a separate vial and dissolved in acetone. 1 wt % (based on the weight of the acrylamide only) diethylamine catalyst is added into the flask containing the TetraThiol1. The acetone/acrylamide mixture is then added dropwise to the TetraThiol1/catalyst mixture at approximately 1 mL/min under mild stirring. The flask is then sealed and allowed to stir overnight. Finally the acetone is distilled off under vacuum at 60° C., leaving a modified TetraThiol1 product.

The resultant modified TetraThiol1 is then combined with 1,3,5-Triallyl-1,3,5-triazine-2,4,6(1H,3H,5H)-trione ("TTT") at a 1:1 molar ratio. 1 wt % photoinitiator (Alpha,alpha-dimethoxy-alpha-phenylacetophenone, aka "DMAP," aka "Irgacure 651") is added to the mixture and then sonicated for 10 minutes or until solution is clear and free of bubbles.

The mixture is then drawn down onto a glass plate at 200 micrometers thickness and cured using 10 passes at 10 ft/min feed speed under a Fusion UV curing line system with a D bulb (400 W/cm2).

[TetraThiol1+Acrylonitrile]+TTT Recipe (tail-group modification): Pentaerythritol tetrakis(3-mercaptopropionate) ("TetraThiol1") is added to a round-bottom flask. An equal molar quantity of acrylonitrile is weighed out in a separate vial. 1 wt % (based on the weight of the acrylonitrile only) diethylamine catalyst is added into the flask containing the TetraThiol1. The acrylonitrile is then added dropwise to the TetraThiol1/catalyst mixture at approximately 1 mL/min under mild stirring. The flask is then sealed and allowed to stir overnight.

The resultant modified TetraThiol1 is then combined with 1,3,5-Triallyl-1,3,5-triazine-2,4,6(1H,3H,5H)-trionc ("TTT") at a 1:1 molar ratio. 1 wt% photoinitiator (Alpha, alpha-dimethoxy-alpha-phenylacetophenone, aka "DMAP," aka "Irgacure 651") is added to the mixture and then sonicated for 10 minutes or until solution is clear and free of bubbles.

The formulation is then drawn down onto a glass plate at 200 micrometers thickness and cured using 10 passes at 10 ft/min feed speed under a Fusion UV curing line system with a D bulb (400 W/cm2).

Example 3

TetraThiol1+TTT +Acrylonitrile Photopolymerization

In this example as shown in Scheme 6, the final film was generated without first reacting one of the thiol groups on the TetraThiol1 as in Example 2 using an amine catalyzed Michael addition. Rather, an excess of the acrylonitrile was mixed into the reaction mixture of the TetraThiol1+TTT such that the total concentration of the acrylonitrile is greater than achieved by first functionalizing one of the thiol groups out of the four thiols in each TetraThiol1 molecule. This eliminates the initial thiol conjugate reaction between one of thiols and the electron poor acrylonitrile group. The result is thought to be a film with greater concentration of converted acrylonitrile units and a higher gas barrier film. It is also different in that some unattached acrylonitrile homopolymer is believed to be present in the final film.

TetraThiol1+Acrylonitrile+TTT Recipe (mixture): Pentaerythritol tetrakis(3-mercaptopropionate) ("TetraThiol 1") is combined with 1,3,5-Triallyl-1,3,5-triazine-2,4,6(1H,3H, 5H)-trione ("TTT") at a 1:1 molar ratio (4:3 functional group ratio). 1 wt % photoinitiator (Alpha,alpha-dimethoxy-alpha-phenylacetophenone, aka "DMAP," aka "Irgacure 651") is added to the mixture along with 2 mol (1:1:2 TetraThiol1:TTT:Acrylonitrile, or 4:3:2 functional group ratio) of acrylonitrile. This mixture is then sonicated for approximately 10 minutes or until solution is clear and free of bubbles.

The mixture is then drawn down onto a glass plate at 200 micrometers thickness and cured using 10 passes at 10 ft/min feed speed under a Fusion UV curing line system with a D bulb (400 W/cm2).

Scheme 6:

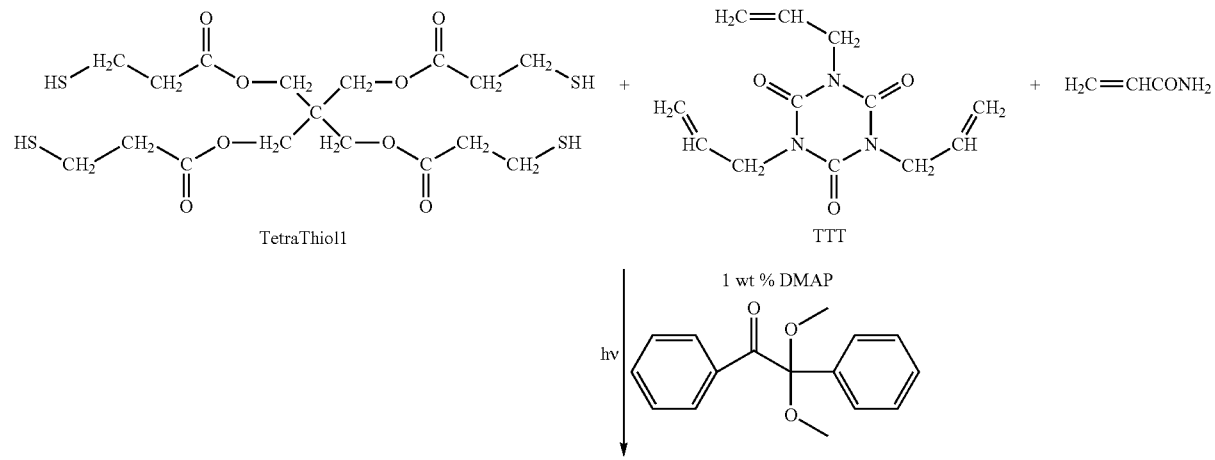

CURED NETWORK FILM

The end product as depicted in Scheme 6 is a network with high connective density formed by sulfides formed by addition of thiols across the carbon-carbon double bonds, i. e., enes. In addition acrylonitrile groups are linked in a chain fashion and incorporated into the network either covalently or alternatively by physical trapping.

Example 4

TetraThiol1+TTT+Fumaronitrile(FN) Photopolymerization

In this example, the final film was generated without pre-reacting one of the thiol groups on the TetraThiol1 as in Example 2 since the Michael addition product of the modified tetrathiol and the fumaronitrile is highly viscous and difficult to incorporate into a formulation. Rather, fumaronitrile was mixed into the reaction mixture of the TetraThiol1+TTT such that the total concentration of the fumaronitrile is equal to that needed to achieve functionalization of one of the thiol groups out of the four thiols in each TetraThiol1 molecule. When a photoinitiator is added to the resulting modified thiol-ene the resulting photopolymerizable formulation is photocured to give a film of high oxygen barrier property.

TetraThiol1+Fumaronitrile+TTT Recipe (mixture): Pentaerythritol tetrakis(3-mercaptopropionate) ("TetraThiol1") is combined with 1,3,5-Triallyl-1,3,5-triazine-2,4,6(1H,3H,5H)-trione ("TTT") at a 1:1 molar ratio (4:3 functional group ratio). 1 wt % photoinitiator (Alpha,alpha-dimethoxy-alpha-phenylacetophenone, aka "DMAP," aka "Irgacure 651") is added to the mixture along with 1 mol (1:1:1 TetraThiol1:TTT:Fumaronitrile, or 4:3:1 functional group ratio) of fumaronitrile. This mixture is then sonicated for approximately 30 minutes or until solution is clear and free of bubbles.

1 wt % diethylamine is then added to the mixture, quickly stirred, and then drawn down onto a glass plate and cured using 10 passes at 10 ft/min feed speed under a Fusion UV curing line system with a D bulb (400 W/cm2). Note that as soon as the diethylamine is added to the mixture, the color turns yellow, viscosity increases, and heat is generated. Also note that this recipe produces a yellow film (unlike each other recipe which produces an optically clear film).

Scheme 7:

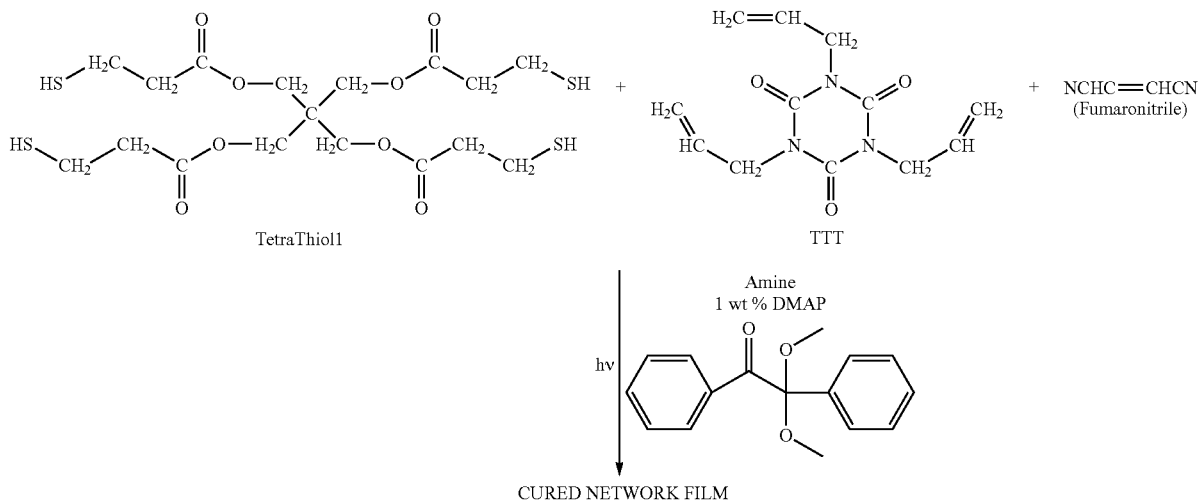

The end product is a network with high connective density formed by sulfides formed by addition of thiols across the carbon-carbon double bonds, i.e., enes. In addition reacted fumaronitrile groups are linked in a chain or non chain fashion and incorporated into the network either covalently or alternatively by physical trapping Prophetic Example 5

Acrylonitrile Polymerization with Multifunctional Acrylate

In this prophetic example, films will be generated by mixing acrylonitrile, TTT, and other multifunctional enes that copolymerize with acrylonitrile to lock in acrylonitrile groups into the matrix and thereby enhance the performance and prohibit any migration of unreacted groups.

Scheme 8:

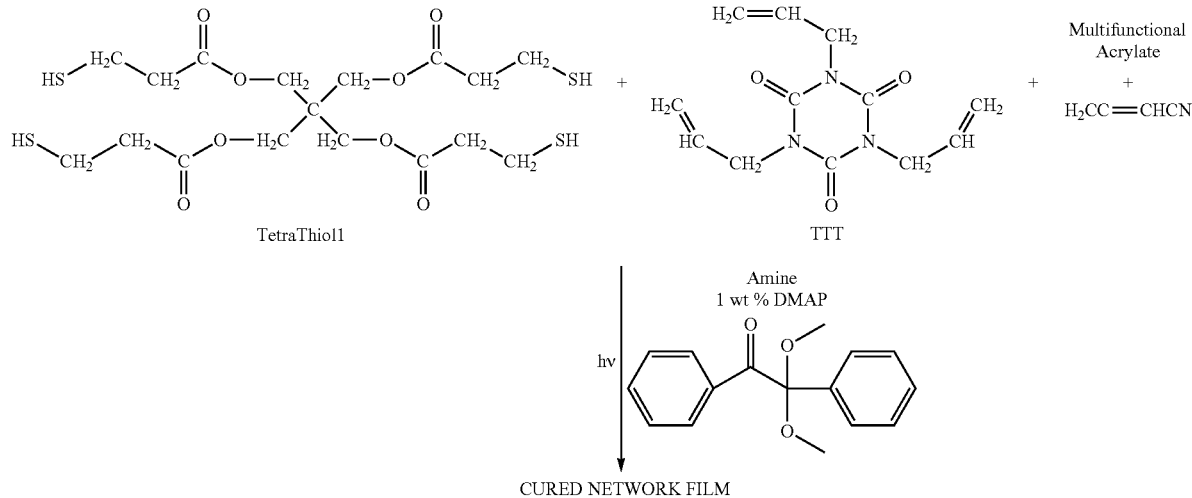

TetraThiol1

TTT

Amine
1 wt % DMAP

CURED NETWORK FILM

The final network will include all enes and acrylonitrile locked into the network matrix chemically either via carbon-carbon single bonds or sulfides.

References

1. S. Pauly, Permeability and diffusion data, in Polymer Handbook, Eds. J. Brandrup, 1999; John Wiley & Sons;
2. W. R. Vieth, Diffusion in and through polymers, Hanser Publishers, New York (1991)
3. J. Comyn, ed., Polymer permeability, Chapman and Hall, New York (1994)
4. P. Neogi, Diffusion in polymers, Marcel Dekker, New York (1996)
5. W. J. Koros, Barrier polymers and structures: overview, in Barrier polymers and structures, W. J. Koros, ed., ASC, Washington, D.C., 1 (1990)
6. D. J. Sekelik, E. V. Stepanov, S. Nazarenko, D. Schiraldi, A. Hiltner, E. Baer, Oxygen barrier properties of crystallized and talc-filled poly(ethylene terephthalate), J. Pol. Sci.: Part B: Polym. Phys., 37, 847 (1999)

What is claimed is:

1. A photopolymerizable formulation comprising:
   a multifunctional thiol, a multifunctional -ene monomer, fumaronitrile and a Michael addition catalyst and optionally a photoiniator.

2. The photopolymerizable formulation of claim 1, wherein the multifunctional thiol is pentaerythritol tetra-(3-mercaptopropionate) (TetraThiol 1), ethoxylated pentaerythritol tetra-(3-mercaptopropionate) (TetraThiol2), trimethylpropane tri(3-mercapto-propionate) (TriThiol 1), glycol 3-merc aptopropionate, poly propylene glycol 3-mercaptopropionate, ethoxylated trimethylpropane tri(3-mercaptopropionate) (TriThiol2), ethoxylated glycol dimercaptoacetate, trimethylolpropane trimercaptoacetate, glycol di-(3-mercaptopropionate), 1,4-bis (3-mercaptobutylyloxy) butane, pentaerithrytol tetrakis (3- mercaptobutylate), tris[2-(3-mercaptopropionyloxy)ethyl] isocyanurate (Trithiol3), or 1,3,5-Tris(3-melcaptobutyloxethyl)-1,3,5-triazine-2,4,6(1H,3H,5H)-trione.

3. The photopolymerizable formulation of claim 1 wherein the multifunctional thiol is pentaerythritol tetrakis(3-mercaptopropionate), the multifunctional -ene monomer is a mixture of 1,3,5-trially-1,3,5-triazine-2,4,6(1H,3H,5H)-trione (TTT) in a 1:1:1 molar ratio of pentaerythritol tetrakis(3-mercaptopropionate):TTT:fumaronitrile.

4. A film of the photopolymerizable formulation of claim 1.

* * * * *